United States Patent
Clarot et al.

(10) Patent No.: US 7,714,011 B2
(45) Date of Patent: *May 11, 2010

(54) COMPOSITIONS TO REDUCE CONGESTION AND METHODS FOR APPLICATION THEREOF TO THE NASAL MEMBRANE

(75) Inventors: Tim Clarot, Phoenix, AZ (US); Charles Hensley, Redondo, CA (US)

(73) Assignee: Zicam, LLC, Scottsdale, AZ (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/663,010

(22) Filed: Sep. 15, 2003
(Under 37 CFR 1.47)

(65) Prior Publication Data
US 2004/0166066 A1   Aug. 26, 2004

Related U.S. Application Data

(60) Provisional application No. 60/410,641, filed on Sep. 13, 2002.

(51) Int. Cl.
| | |
|---|---|
| A01N 43/50 | (2006.01) |
| A01N 31/08 | (2006.01) |
| A61K 8/14 | (2006.01) |
| A61K 8/67 | (2006.01) |
| A61K 31/07 | (2006.01) |
| A61K 31/51 | (2006.01) |
| A61K 31/56 | (2006.01) |
| A61K 31/122 | (2006.01) |
| A61K 31/355 | (2006.01) |
| A61K 31/375 | (2006.01) |
| A61K 31/525 | (2006.01) |
| A61K 31/592 | (2006.01) |
| A61K 31/593 | (2006.01) |
| A61K 31/714 | (2006.01) |
| A61K 31/4415 | (2006.01) |
| A61K 35/60 | (2006.01) |

(52) U.S. Cl. ............ 514/396; 514/168; 514/251; 514/276; 514/458; 514/474; 514/725; 514/731; 424/434; 424/450; 424/487; 424/744

(58) Field of Classification Search ............ 514/168, 514/251, 276, 396, 458, 474, 725, 731; 424/434, 424/450, 487, 744
See application file for complete search history.

(56) References Cited

U.S. PATENT DOCUMENTS

| | | | |
|---|---|---|---|
| 2,115,848 A | 5/1938 | Grant | |
| 4,708,873 A * | 11/1987 | Schulte | 424/744 |
| 4,724,231 A | 2/1988 | Wenig | |
| 4,826,683 A * | 5/1989 | Bates | 424/641 |
| 4,883,660 A | 11/1989 | Blackman et al. | |
| 4,970,240 A | 11/1990 | Kielley | |
| 5,114,979 A | 5/1992 | Kielley | |
| 5,158,761 A | 10/1992 | Kamishita et al. | |
| 5,215,739 A | 6/1993 | Kamishita et al. | |
| 5,240,694 A | 8/1993 | Gwaltney, Jr. | |
| 5,248,501 A | 9/1993 | Parnell | |
| 5,271,943 A | 12/1993 | Bogart et al. | |
| 5,346,703 A | 9/1994 | Viegas et al. | |
| 5,478,565 A | 12/1995 | Geria | |
| 5,492,937 A | 2/1996 | Bogentoft et al. | |
| 5,760,085 A | 6/1998 | Beck et al. | |
| 5,785,988 A | 7/1998 | Fust | |
| 5,854,269 A * | 12/1998 | Haslwanter et al. | 514/385 |
| 5,897,858 A | 4/1999 | Haslwanter et al. | |
| 5,908,619 A | 6/1999 | Scholz | |
| 5,948,414 A | 9/1999 | Wiersma | |
| 5,988,870 A | 11/1999 | Partsky | |
| 6,080,783 A | 6/2000 | Davidson et al. | |
| 6,090,403 A * | 7/2000 | Block et al. | 424/447 |
| 6,143,329 A | 11/2000 | Kim | |
| 6,235,312 B1 | 5/2001 | Hobbs et al. | |
| 6,245,735 B1 * | 6/2001 | Pier | 514/2 |
| 6,316,483 B1 * | 11/2001 | Haslwanter et al. | 514/401 |
| 6,365,624 B1 * | 4/2002 | Davidson et al. | 514/494 |
| 6,375,984 B1 | 4/2002 | Kim | |
| 6,391,294 B1 | 5/2002 | Dettmar et al. | |
| 6,565,832 B1 * | 5/2003 | Haslwanter et al. | 424/45 |
| 6,673,835 B1 * | 1/2004 | Hensley et al. | 514/494 |
| 6,841,146 B2 * | 1/2005 | Haslwanter et al. | 424/45 |
| 6,929,939 B2 * | 8/2005 | Estell et al. | 435/220 |

(Continued)

FOREIGN PATENT DOCUMENTS

| | | |
|---|---|---|
| EP | 0 147 476 A1 | 7/1985 |
| EP | 0 275 054 A1 | 7/1988 |
| EP | 0 391 342 A1 | 10/1990 |
| WO | WO 94/00108 A1 | 1/1994 |
| WO | WO 94/05330 A1 | 3/1994 |
| WO | WO 99/38492 A1 | 8/1999 |
| WO | WO 00/10530 A1 | 3/2000 |

OTHER PUBLICATIONS

Smith et al. Principles of Biochemistry: General Aspects, McGraw-Hill: New York, 1983, pp. 29 and 56-57.*

(Continued)

*Primary Examiner*—Johann R Richter
*Assistant Examiner*—James H. Alstrum-Acevedo
(74) *Attorney, Agent, or Firm*—Snell & Wilmer L.L.P.

(57) ABSTRACT

A gelled composition formulated to maintain an active ingredient in association with the nasal membrane for an extended period of time is provided. The gelled composition may be formulated as a decongestant or a sinus discomfort relieving agent. The invention further includes a system and method for applying the gelled composition to the nasal membrane.

20 Claims, No Drawings

U.S. PATENT DOCUMENTS

| | | | |
|---|---|---|---|
| 7,029,694 | B2* | 4/2006 | Ebert et al. ............... 424/449 |
| 2001/0044411 | A1 | 11/2001 | Gelber et al. |
| 2001/0053775 | A1* | 12/2001 | Seidel et al. ............... 514/179 |
| 2002/0006961 | A1 | 1/2002 | Katz et al. |
| 2002/0012688 | A1 | 1/2002 | Dohi et al. |
| 2002/0022052 | A1 | 2/2002 | Dransfield |
| 2002/0037297 | A1 | 3/2002 | Crespo et al. |
| 2002/0046751 | A1* | 4/2002 | MacRae et al. ......... 128/200.22 |
| 2002/0128273 | A1 | 9/2002 | Gelber et al. |
| 2002/0147232 | A1* | 10/2002 | Sundgreen et al. .......... 514/474 |
| 2002/0172644 | A1 | 11/2002 | Haslwanter et al. |
| 2002/0193417 | A1 | 12/2002 | Seidel et al. |
| 2002/0197212 | A1 | 12/2002 | Osbakken et al. |
| 2003/0031631 | A1 | 2/2003 | Osbakken et al. |
| 2004/0197270 | A1* | 10/2004 | Mundschenk ............... 424/45 |

OTHER PUBLICATIONS

Bastin, R. J. et al. "Salt Selection and Optimisation Procedures for Pharmaceutical New Chemical Entities," Organic Process Research & Development, 2000, 4, 427-435.*

McGraw-Hill Encyclopedia of Science & Technology, 9th edition, McGraw-Hill: New York, 2002, p. 303.*

MacMillan Encyclopedia of Physics, J.S. Rigden, Ed., Simon & Schuster MacMillan: New York, 1996, vol. 4, p. 1677.*

AFRIN® No Drip 12 hr Relief, product information, product purchased Nov. 2, 2008.*

VICK's® Sinex 12-hour Nasal Spray, Online Physician's Desk Reference, accessed Oct. 31, 2008 at www.thomasonhc.com/pdrel/librarian/ND_T/PDRel/ND_CP/Pdr/DocumentID/6540.*

4-Way®, Physician's Desk Reference, 49th edition, Medical Economics Data Production Company: Montvale, NJ, 1995, pp. 705.*

Oxymetazloine (AFRIN®), Drug Information Handbook, Lexi-Comp, Inc.: Cleveland, 1993, pp. 675-676.*

Online search result of the American National Standards Institute (ANSI) website for the ASTM D1824 standard—website accessed on Dec. 4, 2009 at www.astm.org/Standards/D1824.htm.*

Dec. 9, 2009 Fax from Applicants' attorney, Ms. Cynthia L. Pillote, Esq. containing proposed claim amendments and an email dated Nov. 10, 2009 from Mr. Karlos Estevez to Ms. Cynthia Pillote, which evidences that the 1987 revision standard designated as, "ASTM D-1824" (i.e. ASTM D-1824-87 in Applicants' claims) is publicly available.*

* cited by examiner

COMPOSITIONS TO REDUCE CONGESTION AND METHODS FOR APPLICATION THEREOF TO THE NASAL MEMBRANE

CROSS-REFERENCE TO RELATED APPLICATIONS

This application claims the benefit of provisional application Ser. No. 60/410,641, filed Sep. 13, 2002.

FIELD OF INVENTION

The present invention relates generally to a composition formulated to maintain a therapeutically beneficial ingredient in association with the nasal membrane for an extended duration of time, and more specifically, to a composition containing a beneficial ingredient and carrier at a viscosity sufficient to maintain the composition in contact with the nasal membrane for an extended period of time, and methods of applying the same to the nasal cavity.

BACKGROUND OF THE INVENTION

Typical cold and allergy relief remedies are sold in liquid or capsule formulations and are generally administered orally. Although such remedies may work well for relieving some allergy or cold symptoms, the effectiveness of many of these remedies may be limited due to, for example, digestive processes in the oral and digestive pathways. For example, enzymatic activity in the oral cavity and/or acidic environments present in the digestive system may degrade the performance of specific elements or compounds comprising active substances in cold or allergy relief compositions. A further disadvantage of typical compositions involves the circuitous routes some active ingredients are forced to travel, such as when orally administered substances must travel from the oral cavity to the nasal cavity for interaction with active sites in the nasal membrane. For example, these difficulties may be particularly acute when orally administered zinc must travel from the oral cavity up to the ICAM-1 receptor sites on the nasal membrane. Further, effective migration of these active substances may be further impeded when taken by a congested person, often the type of person most in need of these types of nasally bound substances, where the route from the oral cavity to the nasal cavity is blocked or partially blocked by the congestion. Accordingly, a method of delivering active substances to the body which bypasses these degenerative systems is desirable.

Alternative cold and allergy relief techniques involve intravenous administration of the active substances. Such techniques are generally not considered an acceptable commercial alternative to oral application of drugs due to consumer preferences and safety concerns, among others. Transdermal delivery is another alternative delivery method. However, this approach is generally not well suited for all types of active ingredients due to, among others, the significant challenges present in delivery of therapeutically effective amounts of active substances across the epidermal barrier.

Another approach involves nasal cavity administration where active substances are administered directly into the nasal cavity. Many prior attempts at nasal drops and sprays have failed because the active ingredient fails to remain in contact with the nasal membrane for a sufficient period of time, thereby preventing the effective rendering of therapeutically acceptable benefits. For example, typical nasal drops and sprays contain liquid matrices having a low viscosity. Upon application, the liquid tends to be drawn out of the nasal cavity by gravity. The active substance is then prevented from contacting the nasal membrane for an extended period of time sufficient to render a desired therapeutic benefit. For example, some sprays have been observed to dissipate from the nasal cavity in less than five minutes after a first application, which may not allow some active ingredients to remain in contact with the nasal membrane for a sufficient amount of time.

Various methods have been developed attempting to prevent the liquid from dissipating from the nasal cavity, including insertion of cotton swabs and nose plugs into the nasal cavity to prevent leakage. Here too, however, prior methods have proved problematic. Consumers tend to find nose plugs of any type uncomfortable and view them as cosmetically unappealing. Such devices also discourage additional applications of the composition to the nasal membrane as the plug must be removed and reinserted each time. Finally, most plugs tend to contact the nasal membrane directly, which tends to draw the composition away from the nasal membrane due to the absorbent effects of the various materials used to make the plugs.

Accordingly, a composition effective at facilitating contact of an active substance with the nasal membrane for an effective amount of time is needed, and in particular, a composition comprising a decongestant. Moreover, an effective composition and method to deliver an active substance, and in particular a decongestant, to the nasal membrane is also needed.

SUMMARY OF THE INVENTION

While the way in which the present invention addresses the deficiencies and disadvantages of the prior art is described in greater detail hereinbelow, in general, according to various aspects of the present invention, a method and composition are provided for delivering an active substance to the nasal membrane. In accordance with various other aspects of the present invention, the composition is formulated to permit the active substance to remain in contact with the nasal membrane for an extended period of time.

In accordance with one exemplary embodiment of the invention, a composition for application to a nasal membrane is configured to maintain an active substance, such as a decongestant, in contact with the nasal membrane for an amount of time sufficient to permit delivery of a desired amount of active substance to active sites on the nasal membrane, and in further embodiments, across the nasal membrane into the blood or circulatory system of the patient.

In accordance with various aspects, and as further described in greater detail below, the composition includes a gelled delivery matrix, the viscosity of which is formulated to promote extended contact with the nasal membrane while still allowing efficient migration of the active substance across the gelled matrix for delivery to the nasal membrane. In accordance with further embodiments, the active substance may include any substance suitable for promoting a therapeutic benefit, and in particular, may include a decongestant, such as oxymetazoline hydrochloride (HCl).

In accordance with various other aspects of the invention, a system and method for delivering the composition to the nasal membrane is provided. In various embodiments of this aspect of the invention, a spray applicator is provided for insertion into the nasal membrane for administration.

These and other advantages of the various compositions, methods and systems according to various aspects of the present invention will be apparent to those skilled in the art upon reading and understanding the detailed description below.

DETAILED DESCRIPTION OF EXEMPLARY EMBODIMENTS

In accordance with various aspects of the present invention, a composition is provided, which includes a gelled matrix composition and an active substance, and which is formulated to promote maintenance of the active substance in direct contact with the nasal cavity for an extended period of time.

As used herein, an active substance includes any of one or more substances that produces or promotes a beneficial therapeutic, physiological, homeopathic and/or pharmacological effect on the body. Such beneficial effects may be brought upon any animal or human patient, and various systems associated therewith, including the immune system, respiratory system, circulatory system, nervous system, digestive system, urinary system, reproductive system, endocrine system, muscular system, skeletal system, and the like, as well as any organs, tissues, membranes, cells, and subcellular components associated therewith.

As will be appreciated by those skilled in the art, beneficial effects include assisting the more efficient functioning of the various systems described above, such as, for example, helping the body fight sickness and disease, helping the body to heal, etc. Exemplary active substances include any element, composition or material producing A beneficial effect, including vitamins, minerals, nucleic acids, amino acids, peptides, polypeptides, proteins, genes, mutagens, antiviral agents, antibacterial agents, anti-inflammatory agents, decongestants, histamines, anti-histamines, anti-allergens, allergy-relief substances, homeopathic substances, pharmaceutical substances, and the like.

As used herein, a carrier includes any of one or more components of the gelled matrix other than the active substance. In accordance with various embodiments of the invention, the carrier includes at least one fluid component and one thickener component. Exemplary fluid components include any suitable fluid or liquid, such as, for example, water, oil, alcohol, etc. Likewise, the thickener component may include any acceptable thickener (e.g., a substance which increases the viscosity of the composition, causes the composition to gel or coagulate, or the like), such as food-grade or pharmaceutical grade thickeners, including, for example, glycerin, carrageenan, sugar, guar gum, methylcellulose, aloe vera, and the like. In various other embodiments, the carrier may also include other gels, gelling agents, antiseptics, preservatives, permeation enhancers, sequestering agents, buffers, emulsifiers, and any other suitable substance other than the active substance.

In accordance with various embodiments of the present invention, the composition is a homeopathic composition, which includes from about 75% to about 99.999% by weight of at least one carrier and an effective amount of an active substance. The effective amount of the active substance includes any amount of active substance required in a composition or dose suitable to render a beneficial therapeutic effect. For example, in accordance with one aspect of this embodiment, the composition includes from about 0.0000001% to about 5.0% by weight of at least one active substance.

In accordance with various other embodiments, the composition is a pharmaceutical composition, which includes 75% to 99.999% by weight of at least one carrier and an effective amount of an active substance. The effective amount of the active substance includes from about 0.0000001% to about 10% by weight of the composition of at least one active substance.

Exemplary compositions of the present invention have a viscosity from about 2,500 to about 40,000 centipoise. In accordance with various aspects of this embodiment, the compositions have a viscosity from about 3,000 to about 10,000 centipoise, and more preferably from about 4,000 to about 6,000 centipoise. In accordance with various other embodiments, the compositions have a viscosity from about 5,000-40,000 centipoise, preferably about 5,000-7,500 centipoise, and more preferably from about 5,000-6,000 centipoise.

In accordance with one aspect of the invention, the composition is formulated to maintain the settled matrix in association with the nasal cavity for an extended duration. Preferably, this extended duration provides an amount of time sufficient to permit delivery of the active substance to the nasal membrane. When the viscosity is less than about 2,500 centipoise, the composition tends to be drawn out of the nasal cavity by gravity. Compositions exceeding 40,000 centipoise tend to impede transport and delivery of the active substance to the nasal membrane. In some embodiments, the formulation may facilitate maintenance of the matrix in the nasal cavity for about at least ten minutes. In still other embodiments, the formulation may permit maintenance of the matrix in the nasal cavity for about 12 hours.

In accordance with a further aspect of the invention, the present formulation impedes downward flow of the composition out of the nasal cavity due to various counteracting forces, which among others include gravitational forces. During development of the present invention, many currently available nasal sprays were considered and discarded because of the low viscosity of the liquids comprising the sprays. Where a desired composition was delivered to the nasal cavity by a spray applicator, the composition tended to contact the nasal membrane for only a short period, as it dripped out of the nasal cavity shortly after application, usually in less than five minutes. The composition of an exemplary embodiment of the invention overcame this shortcoming of prior art nasal sprays by providing a gelled composition of sufficient viscosity to impede the downward flow of the applied solution out of the nasal cavity thereby facilitating the delivery of an effective amount of active ingredient to the nasal membrane.

In accordance with a further aspect of the present invention, the composition provides an efficient distribution and transport system for delivery of the active substance through the gelled composition to the nasal membrane. In accordance with the present invention, after application of the gelled composition, an interface layer is thought to form between the gelled composition and the nasal membrane. As the active substance is delivered to the nasal membrane, the concentration of the active substance at the interface layer becomes depleted. Due to the unique properties of the gel, additional amounts of the active substance are permitted to travel down the resulting concentration gradient, from higher concentration to lower concentration, to replenish the concentration of the active substance at the interface layer, thereby further driving additional amounts of the active substance into contact with the nasal membrane. This transport system may be impeded however where the viscosity of the gelled composition is too high, such as, for example, where it exceeds 40,000 centipoise.

The gelled composition preferably permits the active substance to diffuse through the composition to the nasal epithelial membrane or mucous of the epithelial membrane. This facilitates the availability of a regular supply of the active substance because diffusion within the composition continues to supply the active substance without requiring that the portion of the composition adjacent to the nasal epithelial membrane (or mucous on the membrane) dissolve or dissipate and expose a fresh portion of the composition containing the active substance. As noted, composition viscosities in excess of about 40,000 centipoise are believed to interfere with the diffusion of active substances through the composition.

Viscosity measurements recited herein were obtained using the Brookfield Syncho-Lectric Viscometer for the measurement of the apparent viscosity of Newtonian and Non-Newtonian materials at low shear rates at given rotation speeds according to ASTM D1824087. See also ASTM D1084-88. As described further hereinbelow, viscosity measurements may be made prior to or after administration of the composition, such as after application from a nasal spray applicator to a selected surface. In accordance with various embodiments of the invention, the composition may thicken after being forced through the spray device, or where the composition is admixed with other components.

In a preferred embodiment of the present invention, the gelled matrix is formed from a carrier composition including from about 0.05% to about 5.0% by weight glycerin. Glycerin is thought to allow ionic active ingredients to remain in an ionic state until contact with the nasal membrane and/or mucous of the nasal membrane.

In accordance with various aspects of the invention, the carrier is formulated to achieve a desired viscosity. In some embodiments, the gelled composition includes from about 75% to about 99.999% by weight of at least one carrier and from about 0.000001% to about 10.0% by weight of an effective amount of an active substance, and more preferably from about 90% to about 99.999% by weight of at least one carrier and from about 0.001 to about 5% of an effective amount of an active substance.

The composition of the carrier, as described above, may include any combination of various liquids, gels, and/or thickeners. In accordance with an exemplary embodiment, the carrier comprises a mixture of purified water and glycerin, for example, 90.0% to 99.0% purified (de-ionized) water, and 0.05 to 5.0% by weight of glycerin. A water and glycerin-based carrier is preferred. Glycerin has many properties that facilitate nasal delivery of drugs and other active substances. For example, glycerin supports certain active substances in an ionic state, as described above, and permits rapid diffusion of various active substances across the gel matrix. Glycerin is also preferred because it has the ability to permeate nasal mucous and the nasal epithelial membrane, while carrying with it the active substance for appropriate delivery.

In accordance with various aspects of the invention, the composition may be formulated for reducing congestion. In this aspect, the active substance preferably comprises a decongestant. Decongestants promote shrinkage of the mucous membrane which makes the breathing process easier, in addition to facilitating drainage of the sinus cavities.

However, in accordance with the present invention, a decongestant may be any substance that promotes drying of nasal mucous, discharge of nasal mucous, and the prevention of formation of new nasal mucous. For example, decongestants may include those selected from a group comprising naphazoline hydrochloride, ephedrine, phenylephrine hydrochloride, oxymetazoline hydrochloride (HCl), xylometaxoline hydrochloride and mixtures thereof. Additionally, many aromatic compounds such as those composed primarily of natural oils or extracts therefrom may be decongestants as well such as camphor, eucalyptus oil, menthol, azulen, extracts thereof, and mixtures thereof. Preferably, the decongestant(s) is present in a concentration from about 0.000001% to about 1.0% by weight.

In accordance with a preferred embodiment, the decongestant comprises at least oxymetazoline hydrochloride (HCl). Preferably this active substance is present at concentrations from about 0.045% to about 0.055% by weight, and more preferably at about 0.05% by weight. In accordance with various embodiments, application of oxymetazoline hydrochloride (HCl) to the nasal cavity provides relief from symptoms related to nasal congestion and sinus pressure nearly immediately and may continue for up to about 12 hours.

Zinc may also act as a decongestant. It is believed that zinc enhances discharge of mucous and inhibits the generation of new mucous. When a gelled matrix comprising zinc is applied to the nasal cavity, zinc ions diffuse from the gel matrix into the mucous or mucous membrane in the nasal cavity. It is believed that the zinc concentration in the mucous or mucous membrane creates a barrier which inhibits viral infection of the nasal epithelial membrane. As ionic zinc is absorbed from the gel into the mucous membrane and other nasal epithelial cells, the gel matrix permits new zinc to diffuse into the nasal membrane. The gel matrix has micelle cell-like properties which facilitate the diffusion of zinc, and other active substances, through the gel matrix. The homeopathic concentration of zinc ions in the zinc gel of the invention is about 4 millimolar (mM) to about 60 millimolar, preferably about 20 mM to about 44 mM. Concentrations of zinc in excess of 44 mM are not preferred unless an antioxidant or other component is included in the gel composition to protect the nasal epithelial membrane from abnormally high concentrations of zinc.

As further described above, the gelled matrix comprises a carrier and active ingredient. The carrier includes any of one or more components of the gelled matrix other than the active substance. For example, the carrier may include thickeners, permeation enhancers, antiseptics, preservatives, buffers, emulsifiers, and any other suitable substance other than the active substance. In various embodiments, the carrier may include at least one fluid component and one thickener component. The fluid component may include any suitable fluid or liquid, such as, for example, water, oil, alcohol, etc.

Likewise, the thickener component or components may be utilized to form colloidal solutions (i.e., suspensions) in order to increase the viscosity of the carrier in the nasal gel composition. Suitable thickeners may include any acceptable thickener, such as food-grade or pharmaceutical-grade thickeners, including, for example, glycerin, carrageenan, sugar, guar gum, methylcellulose, carbohydrate thickeners, aloe barbadensis gel (aloe vera), and the like, as well as other gels, gelling agents, antiseptics, preservatives, permeation enhancers, sequestering agents, buffers, emulsifiers, and the like. The presently preferred concentration for thickeners is 0.000001% to 5.0% by weight.

In accordance with an exemplary embodiment, the composition comprises from about 0.05% to about 2.5% by weight of at least one thickener and preferably about 1.25% by weight of at least one thickener. In accordance with a preferred embodiment, the thickener comprises hydroxycellulose. In accordance with further embodiments, the thickener also comprises from about 0.00001% to about 1.0% by weight of aloe barbadensis gel (200:1 concentrate), and preferably about 0.001% by weight. Addition of aloe barbadensis gel may be preferred where practitioners seek to utilize its soothing properties in a composition. Alternatively, however, aloe may be provided in a suitable delivery formulation that does not significantly increase viscosity, such as, for example, in suitable granulated or powdered forms.

The composition may also include permeation enhancers, which are believed to function by enlarging or loosening tight junctions between cells in the nasal membrane, thereby facilitating passage of the active substance therethrough. Permeation enhancers include liposomes, sequestering agents, ascorbic acid (Vitamin C), glycerol, chitosan, and lysophosphotidylcholin, or any other substance that provides a similar function or result. By way of example, the permeation enhancer may include a sequestering agent, such as EDTA. EDTA is thought to chelate calcium. When applied to the nasal membrane, it is believed to remove calcium from the cell junctions, thereby loosening the junctions to facilitate passage of an active substance therethrough.

Permeation enhancers may be present in any effective amount, with preferably concentrations ranging from about 0.00001% to about 5.0% by weight. In a preferred embodiment, the permeation enhancer includes disodium EDTA, at a concentration of about 0.0001% to about 1.0% by weight, and preferably at about 0.10% by weight.

In accordance with another aspect of the invention, a preservative may be added to the composition to facilitate stability of the various ingredients. Any suitable preservative may be used in accordance with the present invention. Preferably, the preservative includes a 50% solution of benzalkonium chloride, admixed into the composition at a concentration of about 0.0001% to about 0.1% by weight, and preferably about 0.04% by weight. Benzalkonium chloride is also preferred due to its recognized properties as an antiseptic. In a further embodiment, the preservative also comprises an alcohol, and preferably benzyl alcohol, at a concentration of about 0.0001% to about 1.0% by weight, and preferably 0.2% by weight. The preservative may also comprise from about 0.001% to absorb 1.0% by weight and preferably about 0.10% by weight disodium EDTA. It is believed disodium EDTA facilitates stability by combining with metals (chelating) and further by preventing various oxidative processes, as well understood by skilled practitioners in the art.

An emulsion agent, or emulsifier, may also be added to the composition in accordance with the present invention. The emulsifier may be selected from a group containing hydrophobic and hydrophilic substituents, such as glycerolpolyethylene glycol ricinoleate, fatty acid esters of polyethyleneglycol, ethoxylated glycerol, polyethylene glycol, and mixtures thereof. In a preferred embodiment, the emulsifier includes hydroxylated lecithin, present at a concentration from about 0.00001% to about 1.0% by weight, and preferably at about 0.001% by weight.

The composition may also include at least one buffer. Any suitable buffer may be used in accordance with the present invention. In an exemplary embodiment, the composition includes from about 0.0001% to about 3.0% of disodium phosphate (heptahydrate), and preferably about 1.12% by weight, and from about 0.0001% to about 3.0% of monosodium phosphate (monohydrate), and preferably about 2.31% by weight.

In accordance with various aspects of the invention, viscosity may be determined prior to or after application of the composition. For example, it may be desirable to utilize a nasal gel composition which thickens when placed in the nostril of a patient. Utilizing a component which is temperature sensitive and thickens due to the increased temperature in a patient's nose is one avenue of producing an increased viscosity when the nasal gel is applied in the patient's nose. Another avenue is to admix two or more components just prior to applying the nasal gel in the patient's nose. The two components produce a composition having a viscosity greater than either component separately.

The composition of the present invention may be delivered to the nose cavity according to any suitable method, such as a drop applicator, cotton swab, etc. In accordance with a preferred embodiment of the present invention, the composition may be delivered as a spray, which has been determined by the inventors to be a more effective method of treating congestion arising from conditions or illnesses such as colds, flues, and allergies. The method includes the steps of obtaining a composition in accordance with the present invention for delivery into the nasal cavity. The method further includes the step of applying the delivery composition in the nasal cavity with a spray applicator. In further embodiments, the method also includes the step of applying the delivery composition to the nasal cavity such that a first portion of the composition directly contacts at least the nasal membrane, a second portion of the composition directly contacts at least the mucous in the nasal cavity, and a third portion of the composition directly contacts at least the cilia in the nasal cavity.

Practitioners will appreciate that any suitable applicator may be used. In accordance with a preferred embodiment, the applicator is available from Pfeiffer of America, nasal gel pump 61476; address: 12 Roszel Road, Suite C-104, Princeton, N.J. 08540. This applicator is configured to hold about 50 metered 0.125 ml doses, of the composition.

The composition may be delivered to the patient in any suitable dosage. In accordance with one embodiment of the invention, the spray applicator is configured to supply a unit dose of about 0.125 ml of composition to the patient each time a pump associated with the spray applicator is activated (0.125 mls/spray). Preferably, the composition is delivered by applying 2-3 sprays to each nostril.

In accordance with another aspect of the present invention, a method is provided for applying an effective amount of the active substance to the nasal membrane. The method includes the step of providing a viscous delivery composition. An exemplary composition includes 75% to about 99.999% by weight of at least one carrier and less than about 5.0% (e.g., about 1.5 wt %) by weight of the active substance. The composition has a viscosity ranging from about 2,500 centipoise to about 40,000 centipoise, and more preferably from about 4,000 to about 6,000 centipoise. The method includes the additional steps of applying the delivery composition in the nasal cavity in direct contact with the nasal membrane, and maintaining the delivery composition in contact with the nasal membrane for an extended period of time sufficient to deliver an effective amount of active substance to the nasal membrane, for example, at least about ten minutes.

In a further aspect of the invention, a method for reducing the time required to deliver the active substance to the nasal membrane is provided. The method includes the steps of providing at least one carrier; providing at least one active substance; and, providing at least one permeation enhancer to facilitate passage of the active substance into the nasal membrane in the nasal cavity. The method includes the steps of combining the carrier, active substance and permeation enhancer to produce a viscous delivery composition including from about 75% to about 99.999% by weight of the carrier, in addition to an effective amount of the active substance and an effective amount of at least one permeation enhancer. The viscosity of the composition ranges from about 2,500 to about 40,000 centipoise, and more preferably from about 4,000 to about 6,000 centipoise. The method also includes the step of maintaining the delivery composition in contact with the nasal membrane for an extended period of time sufficient to deliver an effective amount of active substance to the nasal membrane, such as, for example, maintaining the composition in contact with the nasal membrane for at least ten minutes. In accordance with these embodiments, enhanced penetration of the active substance into the nasal membrane is facilitated.

EXAMPLE 1

An exemplary gel composition for relieving congestion is prepared by admixing the following ingredients as follows:

| Component | Amount % w/w |
|---|---|
| Oxymetazoline HCL | 0.05% |
| Alkoxylated Diester | 0.001% |
| Aloe Barbadensis Gel (200:1 Concentrate) | 0.001% |
| Benzalkonium Chloride (50% solution) | 0.04% |
| Benzyl Alcohol | 0.20% |
| Disodium EDTA | 0.10% |
| Disodium Phosphate (Heptahydrate) | 1.12% |
| Glycerin | 1.00% |
| Hydroxyethylcellulose | 1.25% |
| Hydroxylated Lecithin | 0.001% |
| Monosodium Phosphate (Monohydrate) | 2.31% |
| Purified Water | 93.927% |

The viscosity of the composition is believed to briefly fluctuate over time, but soon stabilizes at about three (3) months after initial preparation of the gel composition.

For example, viscosity of the above formulation may be as follows:

t(0)=7,000 to 8,000 centipoise;

t(1 month)=4,000 to 5,000 centipoise;

t(2 months)=5,000 to 6,000 centipoise;

t(3 months)=4,500 to 5,000 centipoise;

where t=the time from initial composition preparation, and viscosity is generally stabilized at three (3) months and greater.

EXAMPLE 2

An exemplary gel composition for relieving sinus discomfort is prepared by admixing the following ingredients as follows:

| Component | Amount % w/w |
|---|---|
| Oxymetazoline HCL | 0.05% |
| Menthol | 0.08% |
| Eucalyptus | 0.15% |
| Alkoxylated Diester | 0.001% |
| Aloe Barbadensis Gel (200:1 Concentrate) | 0.001% |
| Benzalkonium Chloride (50% solution) | 0.04% |
| Benzyl Alcohol | 0.20% |
| Disodium EDTA | 0.10% |
| Disodium Phosphate (Heptahydrate) | 1.12% |
| Glycerin | 1.00% |
| Hydroxyethylcellulose | 1.25% |
| Hydroxylated Lecithin | 0.001% |
| Monosodium Phosphate (Monohydrate) | 2.31% |
| Purified Water | 93.927% |

In accordance with a further aspect of the invention, menthol, eucalyptus, and similar compounds may be added to provide relief from sinus discomfort.

EXAMPLE 3

The delivery composition is delivered into the patient's nose using a nasal spray applicator. The patient is instructed to blow her nose prior to administration of the delivery composition. The patient is thereafter instructed to prime the pump associated with the applicator prior to initial use by first removing a safety cap associated therewith, and then holding the bottle upright and pumping the pump applicator several times into a tissue until the pump applicator is primed. The pump applicator is primed where, for example, the gelled composition escapes out of the exterior of the applicator. Preferably, the pump applicator is configured as a metered-dose dispensing bottle configured to provide a specified amount of gelled composition to the patient.

Next, the patient is instructed to place the tip of the nasal pump just past the nasal opening, approximately ⅛ of an inch, and to spray the delivery composition into the nostril by depressing the pump applicator. The patient is instructed to deliver the composition into each nostril.

After application, the patient is instructed to depress the outside of each nostril for about five (5) seconds. The patient is thereafter instructed to reapply the composition to each nostril every two to four (2-4) hours until symptoms subside, and to continue such use for 48 hours.

An effective composition for maintaining an active substance in contact with the nasal membrane for an effective period of time has been presented. In various embodiments, the composition includes a decongestant. The present inventors have advanced the art of delivering active substances to the body by recognizing the advantages of delivering active substances, such as a decongestant, directly to the nasal membrane in a composition formulated with a viscosity sufficient to maintain contact with the nasal membrane for extended durations of time, and further by adding such other ingredients so as to enhance delivery of the active substances, such as permeation enhancers, certain thickeners, cilia activators, and the like.

The present invention has been described above with reference to a number of exemplary embodiments and examples. It should be appreciated that the particular embodiments shown and described herein are illustrative of the invention and its best mode and are not intended to limit in any way the scope of the invention as set forth in the claims. Those skilled in the art having read this disclosure will recognize that changes and modifications may be made to the exemplary embodiments without departing from the scope of the present invention. For example, artisans will recognize that the nasal membrane includes any interior surface of the nasal cavity permitting delivery of an active substance to the body, including the epithelial layer of nasal membrane or mucous of the epithelial layer of the membrane. Further, though reference is made both to "substances" and "ingredients," skilled artisans will further appreciate that the two terms can be used interchangeably. Additionally, although reference is made separately to "gelled matrix," "delivery composition," and "carrier," artisans will understand that these terms may be utilized both individually and interchangeably without departing from the scope of the invention. Although reference has been made throughout to administration of a decongestant, it is intended that the invention be applicable to any suitable active ingredient, such as previously described above. Additionally, though various components of the carrier are described herein in terms of exemplary embodiments, such as, for example, thickeners, permeations enhancers, emulsifiers, buffers, and preservatives, any suitable carrier may be achieved through any number or combination of additives now known or hereafter devised. Accordingly, these and other changes or modifications are intended to be included to be within the scope of the present invention, as expressed in the following claims.

The invention claimed is:

1. A composition for application to a nasal membrane, the composition comprising:
   about 90 to about 99.999 weight percent of a carrier;
   0.000001 to 5.0 wt % thickener comprising one or more compounds selected from the group consisting of glycerin, carrageenan, sugar, guar gum, methylcellulose, and hydroxyethylcellulose;
   about 0.001 to about 5.0 weight percent of at least one active ingredient comprising oxymetazoline hydrochloride; and
   about 0.00001 to about 5.0 weight percent of a permeation enhancer comprising liposomes;
   wherein the composition is a gelled matrix and has a viscosity between about 2,500 and about 40,000 centipoise, as measured according to ASTM D1824-87.

2. A composition for application to a nasal membrane, the composition comprising:
   about 90 to about 99.999 weight percent of a carrier;
   0.000001 to 5.0 wt % thickener comprising one or more compounds selected from the group consisting of glycerin, carrageenan, sugar, guar gum, methylcellulose, and hydroxyethylcellulose;
   about 0.001 to about 5.0 weight percent of at least one active ingredient comprising oxymetazoline hydrochloride;
   about 0.00001 to about 5.0 weight percent of a permeation enhancer comprising liposomes; and
   about 0.000001 to about 1.0 weight percent of an aromatic substance comprising at least one of menthol or eucalyptus oil;
   wherein the composition has a viscosity between about 2,500 and about 40,000 centipoise, as measured according to ASTM D1824-87.

3. A composition for application to a nasal membrane, the composition consisting of:
   about 0.045 wt % to about 0.055 wt % oxymetazoline;
   less than 5.0% by weight of at least one vitamin;
   about 0.00001 wt % to about 5.0 wt % permeation enhancer;
   about 0.000001 wt % to about 1.0 wt % aromatic substance selected from the group consisting of camphor, eucalyptus oil, menthol, azulen, extracts thereof, and mixtures thereof;
   0.00001% to about 1.0% by weight of aloe vera powder;
   about 0.000 1 wt % to about 1.0 wt preservative;
   about 0.000001 to about 5.0 wt % thickener selected from the group consisting of glycerin, carrageenan, sugar, guar gum, methyl cellulose, and hydroxyethylcellulose;
   0.05% to about 5.0% by weight glycerin;
   about 90 wt % to about 99 wt % water;
   about 0.00001 wt % to about 1.0 wt emulsion agent; and
   about 0.0002 wt % to about 6.0 wt % buffer.

4. The composition of claim 3, wherein the composition has a viscosity of about 2,500 cp to about 40,000 cp, as measured according to ASTM D1824-87.

5. The composition of claim 3, wherein the composition has a viscosity of about 3,000 cp to about 10,000 cp, as measured according to ASTM D1824-87.

6. The composition of claim 3, wherein the composition has a viscosity of about 4,000 cp to about 6,000 cp, as measured according to ASTM D1824-87.

7. The composition of claim 3, wherein the composition has a viscosity of about 5,000 cp to about 40,000 cp, as measured according to ASTM D1824-87.

8. The composition of claim 3, wherein the composition has a viscosity of about 5,000 cp to about 7,500 cp, as measured according to ASTM D1824-87.

9. The composition of claim 3, wherein the composition has a viscosity of about 5,000 op to about 6,000 cp, as measured according to ASTM D1824-87.

10. The composition of claim 3, wherein the thickener comprises hydroxyethylcellulose.

11. The composition of claim 3, wherein the composition is in the form of a gelled matrix.

12. The composition of claim 3, wherein the preservative comprises benzyl alcohol, benzalkonium chloride, disodium EDTA, and mixtures thereof.

13. The composition of claim 3, wherein the preservative includes benzyl alcohol, benzalkonium chloride, an disodium EDTA.

14. The composition of claim 3, wherein the permeation enhancer comprises a compound selected from the group consisting of liposomes, sequestering agents, ascorbic acid (Vitamin C), glycerol, chitosan, and lysophosphotidylcholin.

15. The composition of claim 3, wherein the emulsion agent is selected from the group consisting of glycerolpolyethylene glycol ricinoleate, fatty acid esters of polyethyleneglycol, ethoxylated glycerol, polyethylene glycol, and mixtures thereof.

16. The composition of claim 3, wherein the emulsion agent comprises hydroxylated lecithin.

17. The composition of claim 3, wherein the buffer comprises disodium phosphate, monosodium phosphate, or mixtures thereof.

18. The composition of claim 3, wherein the buffer comprises about 0.0001% to about 3.0% of disodium phosphate and 0.0001% to about 3.0% of monosodium phosphate.

19. A method of applying an effective amount of an active substance to a nasal membrane, the method comprising the steps of:
    providing the composition of claim 3;
    applying the composition in the nasal cavity; and
    maintaining the composition in contact with the nasal membrane to reduce one or more symptoms associated with congestion.

20. A composition for application to a nasal membrane, the composition consisting of:
    about 0.045 wt % to about 0.055 wt % oxymetazoline;
    less than 5.0% by weight of at least one vitamin;
    about 0.00001 wt % to about 5.0 wt % permeation enhancer;
    about 0 wt % to about 1.0 wt % aromatic substance selected from the group consisting of camphor, eucalyptus oil, menthol, azulen, extracts thereof, and mixtures thereof;
    0% to about 1.0% by weight of aloe vera powder;
    about 0.0001 wt % to about 1.0 wt % preservative;
    about 0.000001 to about 5.0 wt % thickener selected from the group consisting of glycerin, carrageenan, sugar, guar gum, methylcellulose, and hydroxyethylcellulose;
    0.05% to about 5.0% by weight glycerin;
    about 90 wt % to about 99 wt % water;
    about 0.00001 wt % to about 1.0 wt % emulsion agent; and
    about 0.0002 wt % to about 6.0 wt % buffer.

* * * * *